United States Patent
Schultheiss et al.

(10) Patent No.: US 7,841,995 B2
(45) Date of Patent: Nov. 30, 2010

(54) PRESSURE PULSE/SHOCK WAVE THERAPY METHODS AND AN APPARATUS FOR CONDUCTING THE THERAPEUTIC METHODS

(75) Inventors: Reiner Schultheiss, Illighausen (CH); Wolfgang Schaden, Vienna (AU); John Warlick, Woodstock, GA (US)

(73) Assignee: General Patent, LLC, Marietta, GA (US)

( * ) Notice: Subject to any disclaimer, the term of this patent is extended or adjusted under 35 U.S.C. 154(b) by 206 days.

(21) Appl. No.: 12/246,560

(22) Filed: Oct. 7, 2008

(65) Prior Publication Data
US 2009/0254007 A1    Oct. 8, 2009

Related U.S. Application Data

(62) Division of application No. 11/122,154, filed on May 4, 2005, now Pat. No. 7,470,240.

(51) Int. Cl.
*A61H 1/02* (2006.01)

(52) U.S. Cl. .................... 601/2; 601/4; 600/437

(58) Field of Classification Search .......... 601/2, 601/4; 600/437, 427
See application file for complete search history.

(56) References Cited

U.S. PATENT DOCUMENTS 4,905,671 A    3/1990    Senge et al.

(Continued)

FOREIGN PATENT DOCUMENTS

DE    19721218    11/1998

(Continued)

OTHER PUBLICATIONS

R.Meirer, et al; "Extracorporal shock wave may enhance skin flap survival in an animal model"; British Journal of Plastic Surgery; vol. 58, issue 1, Jan. 2005, pp. 53-57; copyright 2004; The British Assoc of Plastic Surgeons, published by Elsevier Ltd.

(Continued)

*Primary Examiner*—Brian Casler
*Assistant Examiner*—John F Ramirez
(74) *Attorney, Agent, or Firm*—David L. King, Sr.

(57) ABSTRACT

The method of stimulating a substance is disclosed. The method has the steps of activating an acoustic shock wave generator or source to emit acoustic shock waves; and subjecting the substance to the acoustic shock waves stimulating said substance wherein the substance is positioned within a path of the emitted shock waves and away from a geometric focal volume or point of the emitted shock waves. In one embodiment the emitted shock waves are divergent or near planar. In another embodiment the emitted shock waves are convergent having a geometric focal volume of point at a distance of at least X from the source, the method further comprising positioning the substance at a distance less than the distance X from the source. The substance is a tissue having cells. The tissue can be an organ of a mammal. The mammal may be a human or an animal. The organ may be a heart, a brain, skin, a liver or a kidney or any other organ. The tissue may be muscle, cartilage, tendon, bone, teeth or gums. The tissue may be a part of the vascular system, a part of the nervous system, a part of the urinary or reproductive system, a part of the lymph node or pituitary systems, a part of the ocular system or a part of a skeletal system.

20 Claims, 8 Drawing Sheets

U.S. PATENT DOCUMENTS

| | | | |
|---|---|---|---|
| 5,595,178 | A | 1/1997 | Voss et al. |
| 6,068,596 | A | 5/2000 | Weth et al. |
| 6,368,292 | B1 | 4/2002 | Ogden et al. |
| 6,390,995 | B1 | 5/2002 | Odgen et al. |
| 6,755,796 | B2 | 6/2004 | Spector |
| 2002/0002345 | A1 | 1/2002 | Marlinghaus |
| 2003/0129154 | A1 | 7/2003 | McDaniel |
| 2004/0059265 | A1 | 3/2004 | Candy et al. |
| 2004/0162508 | A1 | 8/2004 | Uebelacker |
| 2005/0010140 | A1 | 1/2005 | Forssmann |
| 2005/0038362 | A1 | 2/2005 | Schultheiss |

FOREIGN PATENT DOCUMENTS

| | | |
|---|---|---|
| EP | 0243947 | 4/1987 |
| EP | 0324711 | 1/1989 |
| WO | 2005018600 | 3/2005 |
| WO | 2005063334 | 7/2005 |

OTHER PUBLICATIONS

T.Nishida, et al; "Extracorporeal Cardiac Shock Wave Therapy Markedly Ameliorates Ischemia-Induced Myocardial Dysfunction in Pigs in Vivo"; Circulation; Nov. 9, 2004; Circulation 2004; 110; pp. 3055-3061.

L.Gerdesmeyer, et al; "Antibacterial Effects of Extracorporeal Shock Waves"; World Fed for Ultrasound in Medicine & Biology; printed USA; Elsevier, vol. 31, No. 1, pp. 115-119, 2005.

G.Haupt, et al; "Effect of Shock Waves on the Healing of Partial-Thickness Wounds in Piglets"; Journal of Surgical Research, vol. 49, No. 1, pp. 45-48, Jul. 1990, copyright 1990 by Academic Press, Inc.

Thiel, M et al; "The use of shock waves in medicine-a tool of the modern OR; an overview of basic physical principles, history and research", Min Invas Thar & Allied Technol 2000; 9(3/4) 247-253.

Jagadeesh, G. et al; "Novel applications of micro-shock waves in biological sciences", J.Indian Inst.Sci. 2002, 82, pp. 1-10.

Huemer, Georg M., et al; "Comparison of the effectiveness of gene therapy with transforming growth factor-B or extracorporeal shock wave therapy to reduce ischemic necrosis in an epigastric skin flap model in rats"; Clinical Dept of Plastic and Reconstructive Surgery; Medical University Innsbruck Austria; Feb. 13, 2004; copyrt 2005 by the Wound Healing Society. ISSN: 1067-1927; wound rep reg 2005; 13:262-268.

PRESSURE PULSE/SHOCK WAVE THERAPY METHODS AND AN APPARATUS FOR CONDUCTING THE THERAPEUTIC METHODS

RELATED APPLICATIONS

This is a division of U.S. patent application Ser. No. 11/122,154 entitled "Pressure Pulse/Shock Wave Therapy Methods and an Apparatus for Conducting the Therapeutic Methods" filed on May 4, 2005 which is a continuation in part of U.S. patent application Ser. No. 11/071,156 filed on Mar. 4, 2005 entitled "Pressure Pulse/Shock Wave Apparatus for Generating Waves Having Nearly Plane or Divergent Characteristics" and also claims benefit of priority to U.S. Provisional Patent Application Ser. No. 60/621,028 filed Oct. 22, 2004 and of U.S. Provisional Patent Application Ser. No. 60/642,149 filed Jan. 10, 2005, the disclosures of which are incorporated herein by reference in their entirety.

TECHNICAL FIELD

This invention relates to the field of treating mammals with acoustic pressure pulse shock waves generally. More specifically to treating various conditions found in humans and animals using shock waves that are generated as either focused waves at high or low energy levels or non-focused waves at preferably low energy levels or a combination of such waves.

BACKGROUND OF THE INVENTION

Electro-hydraulic shock wave systems have been used to disintegrate kidney and urethral stones by applying focused shock waves to the stone. A few hundred up to a few thousand shock waves may be required to break a stone within a mammal into small pieces of 3-4 mm diameter which are able to pass over a period of several weeks through the urethra and the bladder out of the patient's body.

Devices using electro-hydraulic (U.S. Pat. No. 4,539,989), piezoceramic (U.S. Pat. No. 5,119,801) or electromagnetic (U.S. Pat. No. 5,174,280) shock wave or pressure pulse generating elements have been described.

The patents used herein to illustrate the invention and, in particular, to provide additional details respecting the practice are incorporated herein by reference in their entirety.

In certain of non-urological applications, shock waves and pressure pulses may be used to treat/cure orthopedic painful conditions. The treated indications may be related to tendons, ligaments, soft tissue and include muscle pain and calcification in tissue. Suitable devices and procedures have been described (U.S. Pat. Nos. 5,545,124 and 5,595,178). Certain unfocused waves have been described in, for example, United States Patent Application 20040162508. The treatment of tissue with shock waves has also been discussed (United States Patent Application 20040162508).

Known devices generally make use of more or less strong focused shock waves which are focused by ellipsoidal reflectors in electro-hydraulic devices (U.S. Pat. No. 4,539,989) or by parabolic reflectors in devices using electromagnetic sources which are emitting waves from a cylindrical surface (U.S. Pat. No. 5,174,280). Other electromagnetic sources may make use of acoustic lenses of different shapes, for example, concave or convex, depending on the sound velocity and density of the lens material used (U.S. Pat. No. 5,419,335 and European Patent 1 445 758 A2). Piezoelectric sources often use spherical surfaces to emit acoustic pressure waves which are self focused to the center of the sphere (U.S. Pat. No. 5,222,484). The same type of focusing has been used in spherical electromagnetic devices (U.S. Pat. No. 4,807,627).

In certain non-urological applications, focused shock waves are used to treat ischemic heart tissue for generating better blood supply by targeting the treated tissue in the focal point of the emitted wave pattern and thus recovering the tissue's functionality as is shown in patent publication US 2002/0002345.

Since 1971 extracorporeal shock wave therapy (hereinafter ESWT) has been used successfully and with a low rate of adverse reactions in the field of urology. Despite the relatively high energy flow densities used during ESWT, no major complications (e.g. malignant degeneration of the treated tissue) have been reported.

The German urologist G. Haupt deserves the credit for the acceptance ESWT has gained in the fields of orthopedics and traumatology as well. Urologists have noticed, that larger amounts of energy (i.e. a larger number of pulses) were required to disintegrate calculi in the urethra and bladder than to break down renal calculi. Initially neither the physicists nor the medical scientists involved in these studies had a plausible explanation for this discrepancy. It was while reviewing follow-up x-rays to detect any recurrences of calculi in patients treated for urethral or bladder stones in 1986 that Haupt first noted a thickening of the ala of the ileum, an anatomical structure lying directly in the path of the shock waves aimed at the calculi. This finding was significant since it indicated that a) bone absorbs shock waves and b) shock waves evidently also trigger biological reactions in bone. Haupt subsequently demonstrated the osteoinductive effect of focused shock waves in animal experiments.

Since it is mainly the physical properties of shock waves that play a central role in the use of extracorporeal shock wave therapy for urological applications, basic research on the use of shock waves for orthopedic and traumatological applications also focused primarily on these dynamic mechanical force related type properties.

This mechanistic model attempts to explain the effect of shock waves in tissue by postulating that the shock wave creates micro lesions in the tissue on which it is concentrated without, however, destroying the surrounding soft-tissue and thus triggers repair processes leading to healing.

This model of action was the reason, moreover, that Schaden et al used high numbers of pulses (i.e. up to 12,000 for treatment of the long bones) when employing shock waves for the first time to treat patients with pseudarthrosis. Several of these treatments had to be terminated after only 3,000 to 4,000 pulses for technical reasons, however, it was noted that the treatment resulted in healing of the patients pseudarthroses despite (or perhaps because of) this circumstance. This observation was congruent with the results of the basic research carried out by M. Maier, who demonstrated that the optimal osteoinductive effect of shock waves on rat femora took place at energy flow densities and pulse numbers which caused practically no histological demonstrable tissue destruction. One consequence of this finding was that basic research on shock waves concentrated increasingly on the biological effects of shock waves.

C. J. Wang discovered that a variety of substances displaying high biological activity are released during and after the application of shock waves to tissue. The production of nitric oxygen (NO), vessel endothelial growth factor (VEGF), bone morphogenetic protein (BMP), and other growth factors have been demonstrated. Furthermore, Maier discovered a decline in the number of small-myelinized neurons after shock wave therapy, an observation that could explain the analgesic effect of shock wave therapy. As a consequence of these findings, the mechanistic model was increasingly relegated to a secondary role and supplanted by a microbiological model explaining the action of shock waves.

In practice the use of ESWT has been a results oriented science wherein a clear and accurate understanding of the actual healing process was neither understood nor fully appreciated. As a result a variety of treatments and uses of ESWT in mammals had heretofore never been tried or attempted or if tried, the outcomes were at best mixed.

A primary factor in the reluctance to use ESWT was that the believed threshold energy requirements were so high that the surrounding tissue would hemorrhage, exhibited by hematomas and bleeding around the treated site. This phenomenon is particularly known in the area of focused emitted waves designed for deep penetration into the patient. US patent publication 2005/0010140 recites the disadvantageous effects of cavitation phenomena can be controlled wherein the shock wave source is connected to a control means which controls the release frequency of shock waves as a function of pulse energy in such a manner that higher pulse energy correlates with lower release frequencies of the shock waves and vice versa. The avoidance of cavitation occurrences would it is postulated result in far less pain for the patient.

The present invention recognizes the underlying beneficial attributes of ESWT are not now and may never be fully comprehended, however, under a more advanced molecular theory the authors of the present invention postulated a microbiological model suggesting the response mechanism to such treatment.

This model attempts to explain the effect of ESWT by postulating neovascularization of the treated tissue with simultaneous release of diverse growth factors. The enhanced metabolic activity taking place in the presence of these growth factors could be responsible for the healing of the chronically inflamed tissue while the decrease in afferent nerve fibers causes the analgesic effect.

The present inventors see that ESWT is a highly versatile therapeutic instrument. It can be used as a bioengineering tool to achieve effects such as the production of growth factors or as a surgical instrument to effect an extremely subtle type of denervation. In the field of traumatology, these properties are used primarily to treat fractures with non-union or delayed osseous union. ESWT is also becoming increasingly important for treating the early stages of osteochondritis dissecans.

It is an object therefore of the present invention to provide a shock wave therapy that employs a more effective wave energy transmission, that is both simple to deploy and less target sensitive when compared to reflected focused waves.

It is a further object of the invention to provide a therapeutic treatment of a large target area for surface or subsurface soft tissues such as skin or near skin conditions or diseases including, but not limited to trauma.

There is a need for an apparatus and a process for optimized electro-hydraulic pressure pulse generation by changing the focusing characteristics of a pressure pulse or shock wave so that focused or unfocused wave fronts with nearly plane acoustic wave front, convergent acoustic wave front or divergent acoustic wave front characteristics can be released by the apparatus.

There is also a need for an apparatus for optimized pressure pulse/shock wave generation, wherein waves with defined wave front characteristics, like focused, nearly plane or divergent are released from the apparatus for treating tissues, in particular, for treating skin or skin near conditions including, but not limited to, skin and skin near conditions caused by trauma or diseases.

There is also a need for providing an apparatus that allows treatment without requiring extensive scanning of the area to be treated. This is usually required to cover an area uniformly if apparatuses using a small focal point are used. Such an apparatus would reduce treatment times.

There is a need for an apparatus that produces waves having nearly plane, convergent or divergent acoustic wave front characteristics with adjustably reducible or reduced energy densities compared to wave fronts emitted by focused shock wave generators having a focal point located directly on the treated tissue.

There is also a need for an apparatus and method that allows using existing pressure pulse generating devices to treat tissues which have more area like than volume like characteristics, such as skin.

These and other applications of the present invention are described more fully as follows with first detailed description of shock wave therapeutic methods and then a detailed description of several shock wave devices and apparati for carrying out the methods.

SUMMARY OF THE INVENTION

The method of stimulating a substance comprises the steps of activating an acoustic shock wave generator or source to emit acoustic shock waves; and subjecting the substance to the acoustic shock waves stimulating said substance wherein the substance is positioned within a path of the emitted shock waves and away from a geometric focal volume or point of the emitted shock waves. In one embodiment the emitted shock waves are divergent or near planar. In another embodiment the emitted shock waves are convergent having a geometric focal volume of point at a distance of at least X from the source, the method further comprising positioning the substance at a distance less than the distance X from the source. The substance is a tissue having cells. The tissue can be an organ of a mammal. The mammal may be a human or an animal. The organ may be a heart, a brain, skin, a liver or a kidney or any other organ. The tissue may be muscle, cartilage, tendon, bone, teeth or gums. The tissue may be a part of the vascular system, a part of the nervous system, a part of the urinary or reproductive system, a part of the lymph node or pituitary systems, a part of the ocular system or a part of a skeletal system.

The method of stimulating a substance can further include a result wherein the step of subjecting the substance to acoustic shock waves stimulates at least some of said cells within said substance to release or produce one or more of nitric oxygen (NO), vessel endothelial growth factor (VEGF), bone morphogenetic protein (BMP) or other growth factors.

The substance can be a tissue having a pathological condition, a tissue having been subjected to a prior trauma, a tissue having been subjected to an operative procedure, or a tissue in a degenerative condition.

The step of subjecting the substance to acoustic shock waves can also include one of the following: the step of correcting a pathological growth of the epiphysial plate; the step of treating cirrhosis of the liver; the step of stimulating wealthy or otherwise enriched cells to fight tumor cells within the tissue; or killing bacteria by destroying bacterial cell membranes or stimulating a biological defense mechanism within said substance by exposure to the acoustic shock waves.

The substance may be a bone that has a non-union which is subjected to the acoustic shock waves to stimulate healing; one or more vertebrae of a spinal column, the spinal column has an indication of spina bifida or other myelodysplasia, the stomach, wherein the stomach has one or more stomach ulcers; a joint and surrounding tissue, having an indication of arthritis or an indication of gout; or a tissue, the tissue exhibiting an indication of diabetes. The bone may have indications of cancer which can be treated using the above method.

The substance may have an indication of rheumatic disease, wherein the rheumatic disease is Lupus; the substance may be skin exhibiting one or more skin sarcomas; the substance may be a tissue exhibiting an indication of cystic fibrosis which is treatable using the above methods.

The substance may be subcutaneous tissue exhibiting cellulitis or other subcutaneous infections.

The substance may be a combination of tissues such as skin and subcutaneous tissue, the substance may include a wound or scar tissue, or include acne or exhibit cellulitis or is skin exhibiting surface irregularities and wherein the exposure to the acoustic shock waves stimulates a skin smoothing reaction.

The substance may be skin and subcutaneous tissue having hair follicles, wherein the exposure to the acoustic shock waves stimulates hair growth.

The substance can be a placenta or a culture of nutrients having stem cells, wherein the shock waves stimulate the stem cells enhancing replications or the human or animal having stem cells within the patient's body whether naturally occurring or artificially introduced which are activated or otherwise stimulated by the exposure to these shock waves.

In another embodiment a method of reducing or eliminating a mass within a substance comprises the steps of: detecting the presence of said mass in said substance, localizing said mass generally within said substance, and stimulating said substance by subjecting low energy divergent, planar or near planar acoustical waves or convergent focused acoustical waves wherein a geometric focal point or volume of the focused waves is not focused at the mass at least for a predetermined time during the step of stimulating the substance.

The method of reducing or eliminating a mass within a substance may further comprise the step of focusing the geometric focal volume or point of convergent high energy acoustical waves on the mass, wherein the step of focusing convergent high energy acoustical waves on the mass generates cellular trauma. The trauma essentially ruptures some cells within said mass thereby reducing or eliminating said mass.

Preferably the substance is tissue having cells and wherein the step of stimulating said substance activates at least some of said cells in proximity to said mass, said cells being enriched with mass destroying agents. The mass destroying agents may include one or more drugs, chemicals or genetic therapeutic agents.

The method of reducing or eliminating a mass within a substance may further comprise the step of: surgically removing at least a portion of the mass or administering one or more drugs to be delivered to the substance or the mass within said substance or irradiating said mass.

As in the prior mentioned method the substance with a mass may be an organ of a mammal, wherein the organ is a brain, heart, kidney, liver, skin or other soft tissued organ and wherein the mass is a tumor.

The substance may be a portion of a skeletal system, a tooth or a gum or other hard tissued substance.

In yet another embodiment the use of shock waves includes a method of preventive shock wave therapy having the steps of: identifying an at risk patient having an at risk tissue; and subjecting the at risk tissue to shock waves to stimulate tissue repair. The step of identifying an at risk patient includes one or more indications of risk based on family history, genetic disposition, physical condition, or blood or tissue analysis. The method of preventive shock wave therapy further may have the step of testing the at risk tissue to establish measured baseline condition pre shock wave therapy and the step of post shock wave therapy testing the treated tissue for comparison to the baseline condition.

In each of these therapeutic methods or treatments using shock waves, the use or treatment may additionally include the use or administration of one or more antibiotics, drugs, chemicals, or other medical treatments to the blood stream stimulated by acoustic shock waves. The overall combination resulting in a reduced healing response time stimulated by the use of acoustic shock waves. In particular the antibiotics or other drugs that are introduced to the blood stream are beneficially assisted by the improved blood supply resulting from being stimulated by these acoustic shock waves. This means the drugs can work faster and be more efficient. The use of such acoustic waves in combination with antibiotics or other drugs means less potent or even lower dosages can be used in most treatments thereby lowering the risk of complications such as liver damage or the like.

The use of acoustic shock wave therapy is particularly important for patients having immune deficiency disorders such as those diagnosed with HIV or AIDs. Similarly smokers and those affected with emphysema. Also cancer patients or those with tumors or melanomas. Leprosy afflicted patients. Periodontal indications or diseases also are beneficially treatable using the above acoustic shock wave therapy. These ailments can be treated by shock wave therapy alone or in combination with other treatments to accelerate the healing process.

In one embodiment, the present invention provides for an apparatus for generating pressure pulse/shock waves comprising: a pressure pulse/shock wave (PP/SW) source, a housing enclosing said PP/SW source, and an exit window from which wave fronts of waves generated by said PP/SW source emanate, wherein said wave fronts have nearly plane or divergent characteristics.

The PP/SW source may comprise a pressure pulse/shock wave generating element for generating pressure pulses/shock waves, a focusing element for focusing the waves into a focus volume outside the focusing element. The apparatus may further comprise a movable elongated mechanical element having a longitudinal axis, wherein said focus volume is situated on or at said longitudinal axis, and said movable elongated mechanical element is movable to extend to or beyond said focus volume so that wave fronts with divergent characteristics emanate from said exit window. The movable elongated element may be part of the housing and the exit window may be a window of the housing. The focusing element may be an acoustic lens, a reflector or a combination thereof.

The PP/SW source may also comprise a pressure pulse/shock wave generating element and waves emanate from the exit window of the housing without being focused by a focusing element.

The PP/SW source may also comprise an electro-hydraulic pressure pulse/shock wave generating element. The element may comprise at least two electrodes. In this case, the PP/SW source may also comprise a generalized paraboloid according to the formula $y^n = 2px$, wherein x and y are Cartesian coordinates, p/2 is a focal point measured from an apex of the generalized paraboloid, and n is about $1.2 < 2$ or $2 < $ about $2.8$, with $n \neq 2$.

The electrodes may be positioned within the generalized paraboloid, and a spark between tips of said electrodes may be, with about +/−5 mm of variance, generated at the focal point p/2 of the generalized paraboloid. The burn down of the electrode tips (z) may be compensated by the selection of (p+/−z) and n so that the resulting generalized paraboloid has a configuration between a paraboloid defined by formula $y^2=2(p+z)x$ and a paraboloid defined by formula $y^2=2(p−z)x$.

The PP/SW source may also comprise an electromagnetic pressure pulse/shock wave generating element. The electromagnetic pressure pulse/shock wave generating element may be an electromagnetic flat or curved emitter emitting waves having nearly plane or divergent characteristics, and wherein the waves emanate from said exit window without being further modified by a lens. The electromagnetic pressure pulse/shock wave generating element may also be an electromagnetic flat emitter emitting waves having nearly plane characteristics. Here, the PP/SW source may further comprise a lens for focusing said waves in a first focal point, wherein divergent waves generated behind said focal point and emanate from the exit window. The PP/SW source may alternatively comprise at least one lens for de-focusing said waves so that waves with divergent wave characteristics emanate from the exit window.

The electromagnetic pressure pulse/shock wave generating element may also be an electromagnetic cylindrical emitter. Here, the PP/SW source may further comprise at least one reflecting element and/or at least one lens.

The PP/SW source may also comprise a piezoceramic pressure pulse/shock wave generating element. The piezoceramic pressure pulse/shock wave generating element may be a piezoceramic flat or curved emitter generating waves having nearly plane or divergent characteristics, and wherein said waves emanate from said exit window without being modified by a lens. The curved emitter may have a curved piezoceramic emitting surface generating waves having divergent characteristics. The piezoceramic pressure pulse/shock wave generating element may also be a piezoceramic flat emitter for emitting waves having nearly plane characteristics. Here, the PP/SW source may further comprise a lens for focusing said waves in a first focal point, wherein divergent waves generated behind said first focal point emanate at said exit window. The PP/SW source may alternatively further comprise at least one lens for de-focusing said waves into divergent waves so that waves with divergent wave characteristics emanate from the exit window.

The piezoceramic pressure pulse/shock wave generating element may also be a piezoceramic cylindrical emitter. Here, the PP/SW source may further comprise at least one reflecting element and/or at least one lens.

Definitions

A "pressure pulse" according to the present invention is an acoustic pulse which includes several cycles of positive and negative pressure. The amplitude of the positive part of such a cycle should be above about 0.1 MPa and its time duration is from below a microsecond to about a second. Rise times of the positive part of the first pressure cycle may be in the range of nano-seconds (ns) up to some milli-seconds (ms). Very fast pressure pulses are called shock waves. Shock waves used in medical applications do have amplitudes above 0.1 MPa and rise times of the amplitude are below 100's of ns. The duration of a shock wave is typically below 1-3 micro-seconds (μs) for the positive part of a cycle and typically above some micro-seconds for the negative part of a cycle.

A "paraboloid" according to the present invention is a three-dimensional reflecting bowl. In two dimensions (in Cartesian coordinates, x and y) the formula $y^2=2px$, wherein p/2 is the distance of the focal point of the paraboloid from its apex, defines the paraboloid. Rotation of the two-dimensional figure defined by this formula around its longitudinal axis generates a de facto paraboloid.

A "generalized paraboloid" according to the present invention is also a three-dimensional bowl. In two dimensions (in Cartesian coordinates, x and y) the formula $y^n=2px$ [with n being ≠2, but being greater than about 1.2 and smaller than 2, or greater than 2 but smaller than about 2.8]. In a generalized paraboloid, the characteristics of the wave fronts created by electrodes located within the generalized paraboloid may be corrected by the selection of (p(−z,+z)), with z being a measure for the burn down of an electrode, and n, so that phenomena including, but not limited to, burn down of the tip of an electrode (−z,+z) and/or disturbances caused by diffraction at the aperture of the paraboloid are compensated for.

Waves/wave fronts described as being "focused" or "having focusing characteristics" means in the context of the present invention that the respective waves or wave fronts are traveling and increase their amplitude in direction of the focal point. Per definition the energy of the wave will be at a maximum in the focal point or, if there is a focal shift in this point, the energy is at a maximum near the geometrical focal point. Both the maximum energy and the maximal pressure amplitude may be used to define the focal point.

"Divergent waves" in the context of the present invention are all waves which are not focused and are not plane or nearly plane. Divergent waves also include waves which only seem to have a focus or source from which the waves are transmitted. The wave fronts of divergent waves have divergent characteristics. Divergent waves can be created in many different way, for example: A focused wave will become divergent once it has passed through the focal point. Spherical waves are also included in this definition of divergent waves and have wave fronts with divergent characteristics.

"Plane waves" are sometimes also called flat or even waves. Their wave fronts have plane characteristics (also called even or parallel characteristics). The amplitude in a wave front is constant and the "curvature" is flat (that is why these waves are sometimes called flat waves). Plane waves do not have a focus to which their fronts move (focused) or from which the fronts are emitted (divergent). "Nearly plane waves" also do not have a focus to which their fronts move (focused) or from which the fronts are emitted (divergent). The amplitude of their wave fronts (having "nearly plane" characteristics) is approximating the constancy of plain waves. "Nearly plane" waves can be emitted by generators having pressure pulse/shock wave generating elements with flat emitters or curved emitters. Curved emitters may comprise a generalized paraboloid that allows waves having nearly plane characteristics to be emitted.

A "curved emitter" is an emitter having a curved reflecting (or focusing) or emitting surface and includes, but is not limited to, emitters having ellipsoidal, parabolic, quasi parabolic (general paraboloid) or spherical reflector/reflecting or emitting elements. Curved emitters having a curved reflecting or focusing element generally produce waves having focused wave fronts, while curved emitters having a curved emitting surfaces generally produce wave having divergent wave fronts.

"AIDS" An acquired defect of cellular immunity associated with infection by the human immunodeficiency virus (HIV), a CD4-positive T-lymphocyte count under 200 cells/microliter or less than 14% of total lymphocytes, and increased susceptibility to opportunistic infections and malignant neoplasms. Clinical manifestations also include emaciation (wasting) and dementia. These elements reflect criteria for AIDS as defined by the CDC in 1993.

"Alzheimer's disease" is a progressive, neurodegenerative disease characterized by loss of function and death of nerve cells in several areas of the brain leading to loss of cognitive function such as memory and language.

"arthritis" An inflammatory condition that affects joints. Can be infective, autoimmune, traumatic in origin.

"bone cancer" a general term to imply malignant tumor growth in bone.

"cancer" a general term for more than 100 diseases that are characterized by uncontrolled, abnormal growth of cells. Cancer cells can spread locally or through the bloodstream and lymphatic system to other parts of the body.

"cellulitis" An acute, diffuse, and suppurative inflammation of loose connective tissue, particularly the deep subcutaneous tissues, and sometimes muscle, which is most commonly seen as a result of infection of a wound, ulcer, or other skin lesions.

"cirrhosis" liver disease characterized pathologically by loss of the normal microscopic lobular architecture, with fibrosis and nodular regeneration. The term is sometimes used to refer to chronic interstitial inflammation of any organ.

"cystic fibrosis" A generalized disorder of infants, children and young adults, in which there is widespread dysfunction of the exocrine glands, characterized by signs of chronic pulmonary disease (due to excess mucus production in the respiratory tract), pancreatic deficiency, abnormally high levels of electrolytes in the sweat and occasionally by biliary cirrhosis. There is an ineffective immunologic defense against bacteria in the lungs.

"diabetes" A heterogeneous group of disorders that share glucose intolerance in common.

"emphysema" a condition in which the walls between the alveoli or air sacs within the lung lose their ability to stretch and recoil. The air sacs become weakened and break. Elasticity of the lung tissue is lost, causing air to be trapped in the air sacs and impairing the exchange of oxygen and carbon dioxide. Also, the support of the airways is lost, allowing for airflow obstruction.

"epiphysial plate" The disc of cartilage between the metaphysis and the epiphysis of an immature long bone permitting growth in length.

"gout" Recurrent acute arthritis of peripheral joints caused by the accumulation of monosodium urate crystals. Often presents as pain and swelling confined to one joint. The big toe joint is commonly affected.

"HIV" Human immunodeficiency virus. Species of LENTIVIRUS, subgenus primate lentiviruses (LENTIVIRUSES, PRIMATE), formerly designated T-cell lymphotropic virus type III/lymphadenopathy-associated virus (HTLV-III/LAV). It is acknowledged to be the agent responsible for the acute infectious manifestations, neurologic disorders, and immunologic abnormalities linked to the ACQUIRED IMMUNODEFICIENCY SYNDROME.

"leprosy" A chronic granulomatous infection caused by *MYCOBACTERIUM LEPRAE*. The granulomatous lesions are manifested in the skin, the mucous membranes, and the peripheral nerves. Two polar or principal types are lepromatous and tuberculoid.

"lupus" is a systemic disease that results from an autoimmune mechanism. Individuals with lupus will produce antibodies to their own body tissues. The resultant inflammation can cause kidney damage, arthritis, pericarditis and vasculitis.

"melanoma" A malignant neoplasm derived from cells that are capable of forming melanin, which may occur in the skin of any part of the body, in the eye, or, rarely, in the mucous membranes of the genitalia, anus, oral cavity, or other sites. It occurs mostly in adults and may originate de novo or from a pigmented nevus or malignant lentigo. Melanomas frequently metastasize widely, and the regional lymph nodes, liver, lungs, and brain are likely to be involved.

"myelodysplasia" is an Abnormal or defective formation of the bone marrow cells and can include such conditions as spina bifida.

"osteoporosis" is a reduction in the amount of bone mass, leading to fractures after minimal trauma.

"periodontal (gum) diseases", including gingivitis and periodontitis, are serious infections that, left untreated, can lead to tooth loss. Periodontal disease is a chronic bacterial infection that affects the gums and bone supporting the teeth.

"pseudoarthrosis" A pathologic entity characterized by deossification of a weight-bearing long bone, followed by bending and pathologic fracture, with inability to form normal callus leading to existence of the "false joint" that gives the condition its name.

"sarcoma" A connective tissue neoplasm formed by proliferation of mesodermal cells; it is usually highly malignant.

"stomach ulcer" Ulceration of the mucous membrane of the stomach.

"rheumatic/rheumatism" A general disease characterized by painful, often multiple, local inflammations, usually affecting the joints and muscles, but also extending sometimes to the deeper organs, as the heart.

BRIEF DESCRIPTION OF THE DRAWINGS

The invention will be described by way of example and with reference to the accompanying drawings in which.

DETAILED DESCRIPTION OF THE INVENTION

Figure 1A:
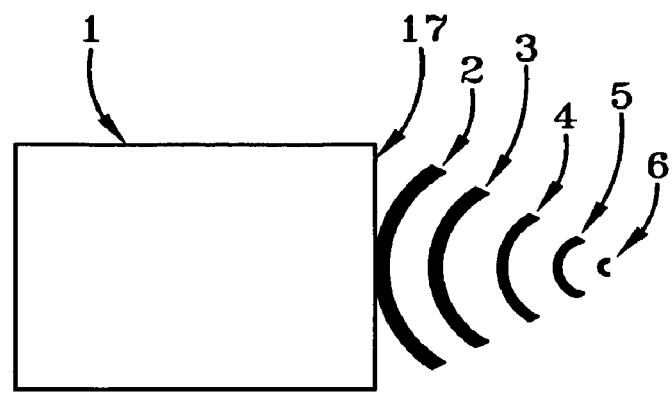
FIG. 1a is a simplified depiction of a pressure pulse/shock wave (PP/SW) generator with focusing wave characteristics.

In the Extracorporeal Shock wave method of treating a mammal be it human or an animal with a known condition to be treated at a target site on the anatomy, the patient is placed in a convenient orientation to permit the source of the emitted waves to most directly send the waves to the target site to initiate shock wave stimulation of the target area. Assuming the target area is within a projected area of the wave transmission, a single transmission dosage of wave energy may be used. The transmission dosage can be from a few seconds to 20 minutes or more dependant on the condition. Preferably the waves are generated from an unfocused or focused source. The unfocused waves can be divergent or near planar and having a low pressure amplitude and density in the range of 0.00001 $mJ/mm^2$ to 1.0 $mJ/mm^2$ or less, most typically below 0.2 $mJ/mm^2$. The focused source preferably can use a diffusing lens or have a far-sight focus to minimize if not eliminate having the localized focus point within the tissue. Preferably the focused shock waves are used at a similarly effective low energy transmission or alternatively can be at higher energy but wherein the tissue target site is disposed pre-convergence inward of the geometric focal point of the emitted wave transmission.

These shock wave energy transmissions are effective in stimulating a cellular response and can be accomplished without creating the cavitation bubbles in the tissue of the target site. This effectively insures the patient does not have to experience the sensation of pain so common in the higher energy focused wave forms having a focal point at or within the targeted treatment site.

Accordingly unless for other reasons such as a trauma or immediate post operative shock wave therapy no localized or general anesthesia is required.

If the target site is an organ within the body cavity the target site may be such that the patient or the generating source must be reoriented relative to the site and a second, third or more treatment dosage can be administered. The fact that the dosage is at a low energy the common problem of localized hemorrhaging is reduced making it more practical to administer multiple dosages of waves from various orientations to further optimize the treatment and cellular stimulation of the target site. Heretofore focused high energy multiple treatments induced pain and discomfort to the patient. The use of low energy focused or un-focused waves at the target site enables multiple sequential treatments. Alternatively the wave source generators may be deployed in an array wherein the subject patient is effectively enveloped or surrounded by a plurality of low energy wave source generators which can be simultaneously bombarding the target site from multiple directions.

Ideally in treating large surface or subsurface tissue such as the skin the patient can be supported on a wave transmitting bed or gel with the movement of one or more low energy wave sources being selectively moved to cover the entire target area.

Accordingly the patient or the array of generators can be moved relative to the other such that the transmitted waves can impinge the targeted site without disturbing or requiring a manipulation of the patient These beneficial adaptations of the use of a bank or array of multiple wave form generators was not practical in the use of focused high energy wave forms because the convergence of the emitted waves impinged on a very small area at a precise depth accordingly the optimal target orientations would be selected and as in the case of planters warts ideally reorientation of the generating source could be avoided. The goal in such treatments was to provide 2000 to 6000 acoustic shock waves at a voltage of 14 kV to 28 kV across a spark gap generator in a single treatment preferably or one or more adjuvant treatments by precisely targeting the site impinging the focal point on the target.

The present method does not rely on precise site location per se. The physician's general understanding of the anatomy of the patient should be sufficient to locate the target area to be treated. The treated area can withstand a far greater number of shock waves based on the selected energy level being emitted. For example at very low energy levels the stimulation exposure can be provided over prolonged periods as much as 20 minutes if so desired. At higher energy levels the treatment duration can be shortened to less than a minute, less than a second if so desired. The limiting factor in the selected treatment dosage is avoidance or minimization of cell hemorrhaging and other kinds of damage to the cells or tissue while still providing a stimulating cellular release or activation of VEGF and other growth factors.

Due to the wide range of beneficial treatments available it is believed preferable that the optimal use of one or more wave generators or sources should be selected on the basis of the specific application. Wherein relatively small target sites may involve a single wave generator placed on an adjustable manipulator arm, whereas large organs such as a patient's skin may be best treated using an array of two or more such generators, these arrays being computer controlled or otherwise enabled to permit either sequential or simultaneous wave bombardment of the target site. The use of such arrays can reduce patient dosage treatment time over very large areas to a matter of a few minutes or less. The ideal treatment therapy should be less than 20 minutes, preferably less than 5 minutes to insure patient inconvenience is minimized while maximizing patient comfort.

A key advantage of the present inventive methodology is that it is complimentary to conventional medical procedures. In the case of any post operative surgical procedure the surgical area of the patient can be post operatively bombarded with these low energy waves to stimulate cellular release of healing agents and growth factors. This will dramatically reduce the healing process. Most preferably such patients may be provided more than one such ESWT treatment with an intervening dwell time for cellular relaxation prior to secondary and tertiary treatments.

The underlying principle of these shock wave therapy methods is to stimulate the body's own natural healing capability. This is accomplished by deploying shock waves to stimulate strong cells in the tissue to activate a variety of responses. The acoustic shock waves transmit or trigger what appears to be a cellular communication throughout the entire anatomical structure, this activates a generalized cellular response at the treatment site, in particular, but more interestingly a systemic response in areas more removed from the wave form pattern. This is believed to be one of the reasons molecular stimulation can be conducted at threshold energies heretofore believed to be well below those commonly accepted as required. Accordingly not only can the energy intensity be reduced but also the number of applied shock wave impulses can be lowered from several thousand to as few as one or more pulses and still yield a beneficial stimulating response.

In the treatment of osteoporosis the bone porosity is a damaged hip for example treated with a shock wave therapy increases in density. What is a more remarkable finding is that a 3% to 4% increase in bone density of the opposite, non-treated hip occurs. This evidences the systemic response of the bone skeletal system is beneficially activated in a location removed from the targeted site at a cellular level demonstrating a form of cellular communication is occurring.

The use of shock waves as described above appears to involve factors such as thermal heating, light emission, electromagnetic field exposure, chemical releases in the cells as well as a microbiological response within the cells. Which combination of these factors plays a role in stimulating healing is not yet resolved. However, there appears to be a commonality in the fact that growth factors are released which applicants find indicative that otherwise dormant cells within the tissue appear to be activated which leads to the remarkable ability of the targeted organ or tissue to generate new growth or to regenerate weakened vascular networks in for example the cardio vascular system. This finding leads to a complimentary use of shock wave therapy in combination with stem cell therapies that effectively activate or trigger stem cells to more rapidly replicate enhancing the ability to harvest and culture more viable cells from the placenta, a nutrient culture of said stem cells, or other sources. The ability to stimulate stem cells can occur within the patients own body activating the naturally occurring stem cells or stem cells that have been introduced to the patient as part of a treatment beneficially utilizing stem cells. This is a significant clinical value in its own right.

The invention as described herein directly relates to the stimulation of healing in all kinds of tissue and organs, and regeneration or generation of nerves, cartilage, skin, bone, muscle, tendon or vascularization. In one embodiment, the invention provides for germicidal cleaning of diseased or infected areas and for wound cleaning generally.

The invention has a variety of advantageous uses in cosmetics such as reduction of cellulitis, scar tissue, acne and skin smoothing as well as hair growth stimulation and skin flap healing.

The methodology and associated apparatus have a variety of clinically beneficial features that can enhance the treatment of diseases such as cancer or cirrhosis of the liver.

The use of extracorporeal shock wave therapy requires a fundamental understanding of focused and unfocused shock waves, coupled with a more accurate biological or molecular model.

Focused shock waves are focused using ellipsoidal reflectors in electromechanical sources from a cylindrical surface or by the use of concave or convex lenses. Piezoelectric sources often use spherical surfaces to emit acoustic pressure waves which are self focused and have also been used in spherical electromagnetic devices.

Concrement disintegration and stimulation of Pseudarthroses gaps directs the shock wave energy at limited spatial areas. High pressure amplitudes and energies need to exceed certain thresholds of stone material for mechanical disintegration work. Accordingly the generation of fractures within the medullar bone explained the stimulation of healing proportional to the acoustic energy. Recent clinical studies conducted by the inventors of this application have produced findings that reveal identical or even better outcomes at low number of shocks.

The biological model proposed by co-inventor Wolfgang Schaden provides a whole array of clinically significant uses of shock wave therapy.

Accepting the biological model as promoted by W. Schaden, the peak pressure and the energy density of the shock waves can be lowered dramatically. Activation of the body's healing mechanisms will be seen by in growth of new blood vessels and the release of growth factors.

The biological model motivated the design of sources with low pressure amplitudes and energy densities. First: spherical waves generated between two tips of an electrode; and second: nearly even waves generated by generated by generalized parabolic reflectors. Third: divergent shock front characteristics are generated by an ellipsoid behind F2. Unfocused sources are preferably designed for extended two dimensional areas/volumes like skin. The unfocused sources can provide a divergent wave pattern or a nearly planar wave pattern and can be used in isolation or in combination with focused wave patterns yielding to an improved therapeutic treatment capability that is non-invasive with few if any disadvantageous contraindications. Alternatively a focused wave emitting treatment may be used wherein the focal point extends preferably beyond the target treatment site, potentially external to the patient. This results in the reduction of or elimination of a localized intensity zone with associated noticeable pain effect while providing a wide or enlarged treatment volume at a variety of depths more closely associated with high energy focused wave treatment. The utilization of a diffuser type lens or a shifted far-sighted focal point for the ellipsoidal reflector enables the spreading of the wave energy to effectively create a convergent but off target focal point. This insures less tissue trauma while insuring cellular stimulation to enhance the healing process.

This method of treatment has the steps of, locating a treatment site, generating either convergent diffused or far-sighted focused shock waves or unfocused shock waves, of directing these shock waves to the treatment site; and applying a sufficient number of these shock waves to induce activation of one or more growth factor thereby inducing or accelerating healing.

The unfocused shock waves can be of a divergent wave pattern or near planar pattern preferably of a low peak pressure amplitude and density. Typically the energy density values range as low as 0.000001 $mJ/mm^2$ and having a high end energy density of below 1.0 $mJ/mm^2$, preferably 0.20 $mJ/mm^2$ or less. The peak pressure amplitude of the positive part of the cycle should be above 1.0 and its duration is below 1-3 microseconds.

The treatment depth can vary from the surface to the full depth of the human or animal torso and the treatment site can be defined by a much larger treatment area than the 0.10-3.0 $cm^2$ commonly produced by focused waves. The above methodology is particularly well suited for surface as well as sub-surface soft tissue treatments.

The above methodology is valuable in generation of tissue, vascularization and may be used in combination with stem cell therapies as well as regeneration of tissue and vascularization.

The methodology is useful to treat pathological, post traumatically, post operative or degenerative nerve damage via nerve (re)generation. In particular where the nerves are damaged the method of treating the damaged nerves within the tissue include subjecting the nerves to shock waves to heal, regenerate or find nerve ends. The patients in this type of therapy may have a mild indication of paraplegia involving some loss of feeling to severe indications such as partial or complete paralysis caused by severed nerves.

The methodology is useful to treat post operative, post traumatically, or degenerative osteoarthritis via cartilage (re)generation.

The methodology is useful in skin (re)generation to treat venous, arterial, diabetic, decubital, post operative, post traumatically or post burning.

The methodology is useful in bone (re)generation to treat maxillary, mandible or skeletal system post operative, post traumatically or degenerative.

The methodology is useful in muscle or tendon (re)generation to treat pathological, post traumatically, post operative or degenerative.

The methodology is useful in (re)vascularization of organs in the heart, brain, liver, kidney and skin.

The methodology is useful in the treatment of cancer by stimulating healthy cells to attack the tumorous cell thereby inhibiting the spread of the cancer. When further combined with a focused shock wave therapy the tumorous growth or mass can be targeted and weakened cellularly followed by a stimulation of near proximity healthy cancer free cells to invasively destroy the tumor.

The methodology is useful in stimulating enforcement of defense mechanisms in tissue cells to fight infections from bacteria and can be used germicidally to treat or cleanse wounds or other target sites.

The methodology can be further used to correct pathological growth of the epiphyseal plate.

Conditions caused by cirrhosis of the liver can be treated by reversing this degenerative condition. Similarly gum disease can be treated using the above methodology.

The methodology lends itself to cosmetic uses in eliminating or reducing cellulitis, scar tissue, acne, and skin smoothing as well as for stimulating hair growth.

While the above listed indications cited above are not exhaustive nor intended to be limiting, it is exemplary of the wide range of beneficial uses of low energy and amplitude unfocused divergent or nearly planar shock waves, convergent shock waves, diffused shock waves or a combination of shock wave types in the treatment of humans and other mammals.

While one of the benefits of the non-invasive nature of this treatment relates to reducing patient recovery and healing time, the fact that the treatments can be delivered at dosages well below the threshold of pain means that no local or general anesthesia is typically required as a consequence of the treatment. This alone significantly reduces any risk factors or complications associated with pain management during the procedure. The treatments further can reduce the need for a regiment of chemical or drug therapies before or after exposure to this shock wave therapy. Alternatively, ESWT can be used in conjunction with chemical or drug therapies to increase the cellular response permitting an opportunity to lower dosages of such chemicals or drugs while increasing the therapeutic efficiency. This is a particularly useful tool for the physician whose patient is elderly, a smoker or with an immune system deficiency which would complicate if not make unavailable more traditional invasive surgical procedures. In fact the above methodology proposed in this patent may be the first if not only choice of treatment available for patients in this class wherein heretofore conventional procedures were deemed too risky.

A further clinical benefit of the above methodology is that the procedure can be done either as an outpatient treatment or at a doctor's office assuming the patient's condition does not otherwise require hospitalization.

A most significant method of preventive medicine can be practiced that is fully enabled by the use of these relatively low amplitude and pressure shock waves. The method includes the steps of identifying high risk patients for a variety of potential conditions. Such condition could be by way of example heart disease caused by poor vascularization. After identifying a risk prone candidate providing one or a series of two or more exposure treatments with unfocused, divergent or near planar shock waves or convergent far-sighted focused shock waves or diffused shock waves to the treatment site, in this example the heart. Then after treatments the physician can optionally ultrasound visually or otherwise determine the increase in vascularization after a period of time. Assuming an initial baseline determination of the heart vascularization had been initially conducted an estimate or calculation of improved vascularization of the site can be made. This procedure can be used for any at risk condition.

The implications of using the (re)generative features of this type of shock wave therapy are any weakened organ or tissue even bone can be strengthened to the point of reducing or eliminating the risk of irreparable damage or failure.

The stimulation of growth factors and activation of healing acceleration is particularly valuable to elderly patients and other high risk factor subjects.

Additionally the ability to stimulate tissue, nerve and bone generation may find valuable uses in reattachment of limbs wherein post operative healing can be given a marked increase in successfully gaining full use of a reattached limb. Similar gains are visualized in organ transplant and complete organ regeneration.

Even more striking as mentioned earlier, early prevention therapies can be employed to stimulate tissue or organ modeling to be maintained within acceptable ranges prior to a degeneration occurring. This is extremely valuable in the prevention of heart disease for example. The methods would be to identify at risk patients based on family history or genetic disposition, physical condition, etc. and subjecting that patient to therapeutic shock wave therapy for the purpose of stimulating tissue repair effectively remodeling the patient's susceptible organ to be within accepted functional parameters. The objective being to preventively stimulate cellular tissue repairs to preemptively avoid a degenerative condition from occurring which may require invasive surgical procedures.

This preventive therapy is most needed to combat neurological degenerative conditions such as alzheimer's disease or brain trauma injuries. Kidney failure indications can similarly be pre-screened for susceptibility as well as the liver for cirrhosis and the heart for vascularization or any other degenerative condition.

The use of the proposed shock wave therapy further can provide tremendous relief to burn victims. Shock wave treated skin tissue can be more rapidly regenerated or generated for skin grafting and the germicidal cleansing effect of low energy unfocused shock waves on the patient can help reduce the infection caused by the damaged tissue while promoting tissue attachment and healing of the grafted skin.

Applicants have applied this treatment therapy to cartilage and tendon orthoscopic repairs and have reduced the healing time from over 6 weeks to less than 2 weeks. These and other beneficial treatments are made possible by using an apparatus with a shock wave emission either singularly or in an array as described below in the embodiments shown in FIGS. 1-12

FIG. 1a is a simplified depiction of the a pressure pulse/shock wave (PP/SW) generator, such as a shock wave head, showing focusing characteristics of transmitted acoustic pressure pulses. Numeral 1 indicates the position of a generalized pressure pulse generator, which generates the pressure pulse and, via a focusing element, focuses it outside the housing to treat diseases. The diseased organ is generally located in or near the focal point which is located in or near position 6. At position 17 a water cushion or any other kind of exit window for the acoustical energy is located.

Figure 1B:
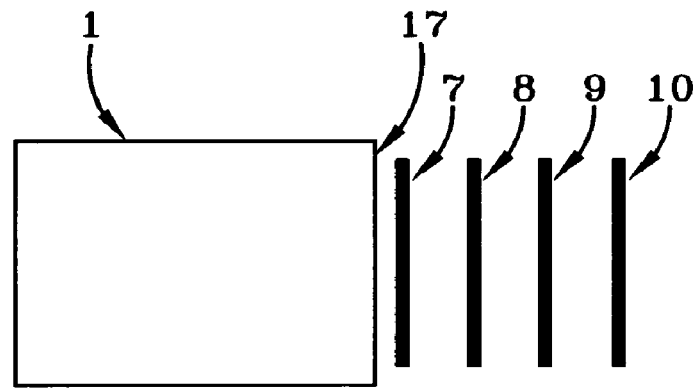
FIG. 1b is a simplified depiction of a pressure pulse/shock wave generator with plane wave characteristics.

FIG. 1b is a simplified depiction of a pressure pulse/shock wave generator, such as a shock wave head, with plane wave characteristics. Numeral 1 indicates the position of a pressure pulse generator according to the present invention, which generates a pressure pulse which is leaving the housing at the position 17, which may be a water cushion or any other kind of exit window. Somewhat even (also referred to herein as "disturbed") wave characteristics can be generated, in case a paraboloid is used as a reflecting element, with a point source (e.g. electrode) that is located in the focal point of the paraboloid. The waves will be transmitted into the patient's body via a coupling media such as, e.g., ultrasound gel or oil and their amplitudes will be attenuated with increasing distance from the exit window 17.

Figure 1C:
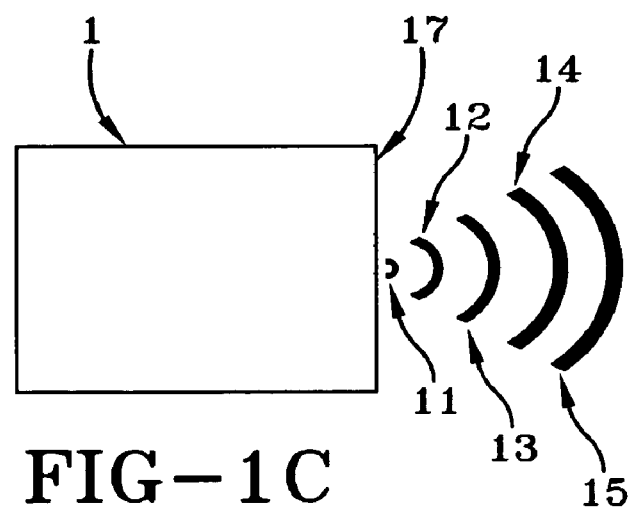
FIG. 1c is a simplified depiction of a pressure pulse/shock wave generator with divergent wave characteristics.

FIG. 1c is a simplified depiction of a pressure pulse shock wave generator (shock wave head) with divergent wave characteristics. The divergent wave fronts may be leaving the exit window 17 at point 11 where the amplitude of the wave front is very high. This point 17 could be regarded as the source point for the pressure pulses. In FIG. 1c the pressure pulse source may be a point source, that is, the pressure pulse may be generated by an electrical discharge of an electrode under water between electrode tips. However, the pressure pulse may also be generated, for example, by an explosion. The divergent characteristics of the wave front may be a consequence of the mechanical setup shown in FIG. 2b.

Figure 2A:
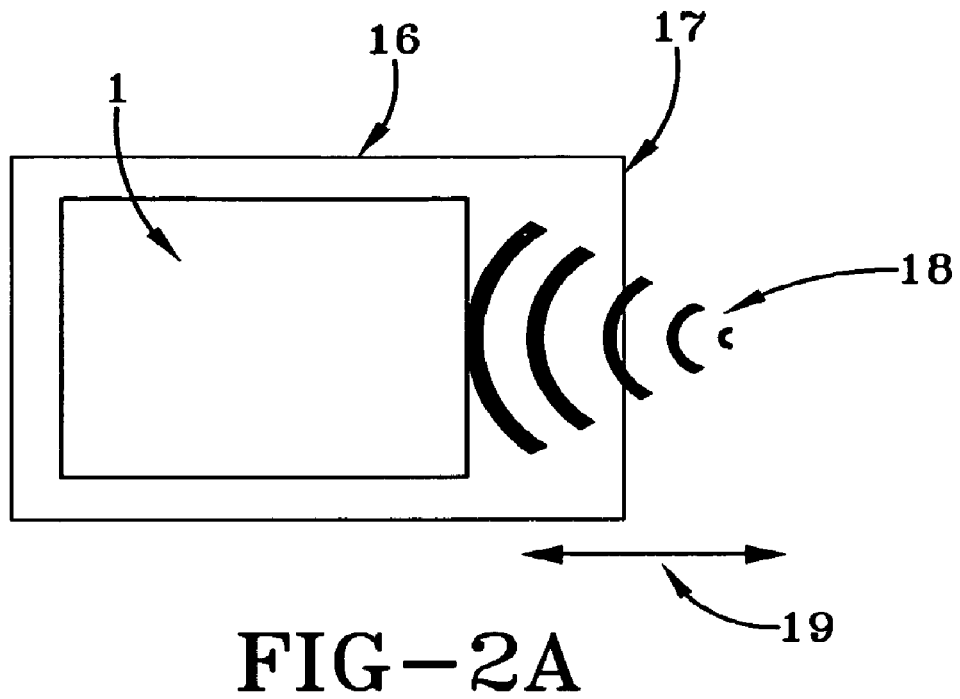
FIG. 2a is a simplified depiction of a pressure pulse/shock wave generator having an adjustable exit window along the pressure wave path. The exit window is shown in a focusing position.

FIG. 2a is a simplified depiction of a pressure pulse/shock wave generator (shock wave head) according to the present invention having an adjustable or exchangeable (collectively referred to herein as "movable") housing around the pressure wave path. The apparatus is shown in a focusing position. FIG. 2a is similar to FIG. 1a but depicts an outer housing (16) in which the acoustical pathway (pressure wave path) is located. In a preferred embodiment, this pathway is defined by especially treated water (for example, temperature controlled, conductivity and gas content adjusted water) and is within a water cushion or within a housing having a permeable membrane, which is acoustically favorable for the transmission of the acoustical pulses. In certain embodiments, a complete outer housing (16) around the pressure pulse/shock wave generator (1) may be adjusted by moving this housing (16) in relation to, e.g., the focusing element in the generator. However, as the person skilled in the art will appreciate, this is only one of many embodiments of the present invention. While the figure shows that the exit window (17) may be adjusted by a movement of the complete housing (16) relative to the focusing element, it is clear that a similar, if not the same, effect can be achieved by only moving the exit window, or, in the case of a water cushion, by filling more water in the volume between the focusing element and the cushion. FIG. 2a shows the situation in which the arrangement transmits focused pressure pulses.

Figure 2B:
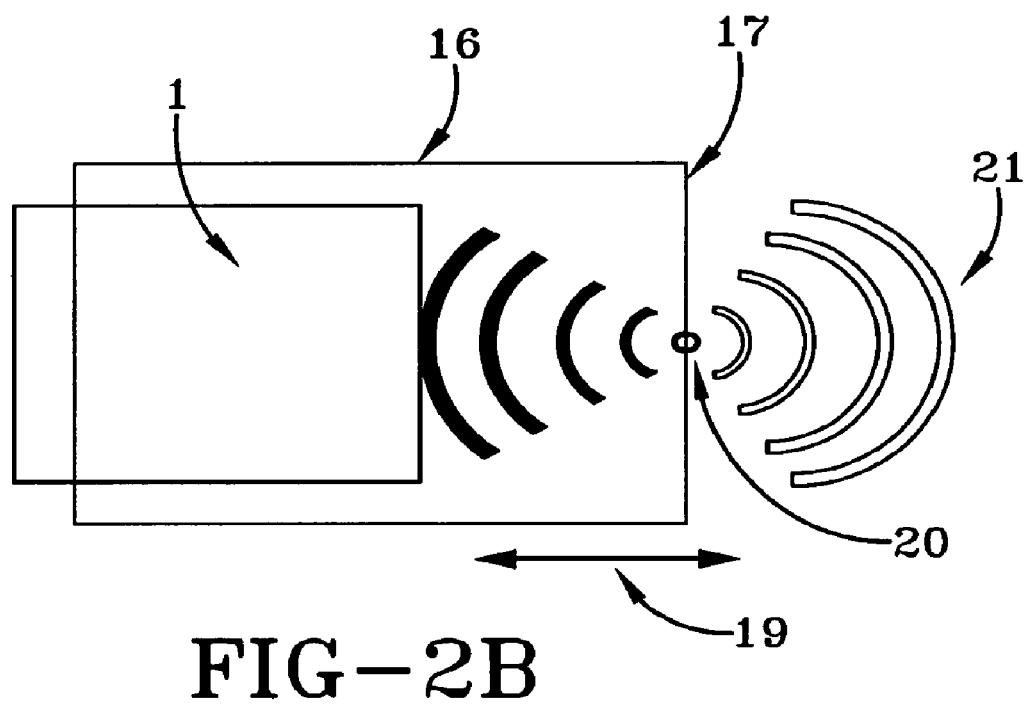
FIG. 2b is a simplified depiction of a pressure pulse/shock wave generator having an exit window along the pressure wave path. The exit window as shown is positioned at the highest energy divergent position.

FIG. 2b is a simplified depiction of the pressure pulse/shock wave generator (shock wave head) having an adjustable or exchangeable housing around the pressure wave path with the exit window 17 being in the highest energy divergent position. The configuration shown in FIG. 2b can, for example, be generated by moving the housing (16) including the exit window (17), or only the exit window (17) of a water cushion, towards the right (as shown in the Figure) to the second focus f2 (20) of the acoustic waves. In a preferred embodiment, the energy at the exit window will be maximal. Behind the focal point, the waves may be moving with divergent characteristics (21).

Figure 2C:
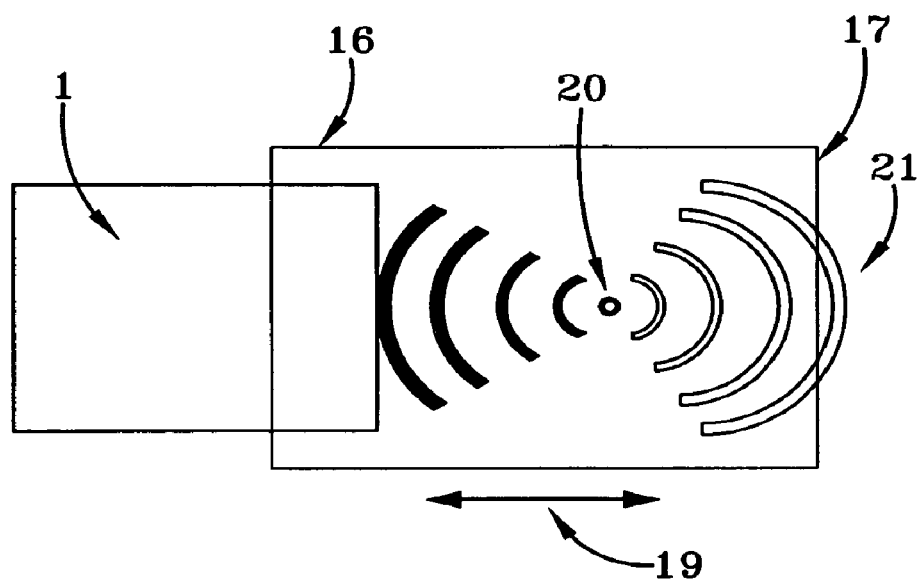
FIG. 2c is a simplified depiction of a pressure pulse/shock wave generator having an exit window along the pressure wave path. The exit window is shown at a low energy divergent position.

FIG. 2c is a simplified depiction of the pressure pulse/shock wave generator (shock wave head) having an adjustable or exchangeable housing around the pressure wave path in a low energy divergent position. The adjustable housing or water cushion is moved or expanded much beyond f2 position (20) so that highly divergent wave fronts with low energy density values are leaving the exit window (17) and may be coupled to a patient's body. Thus, an appropriate adjustment can change the energy density of a wave front without changing its characteristic.

This apparatus may, in certain embodiments, be adjusted/modified/or the complete shock wave head or part of it may be exchanged so that the desired and/or optimal acoustic profile such as one having wave fronts with focused, nearly plane or divergent characteristics can be chosen.

A change of the wave front characteristics may, for example, be achieved by changing the distance of the exit acoustic window relative to the reflector, by changing the reflector geometry, by introducing certain lenses or by removing elements such as lenses that modify the waves produced by a pressure pulse/shock wave generating element. Exemplary pressure pulse/shock wave sources that can, for example, be exchanged for each other to allow an apparatus to generate waves having different wave front characteristics are described in detail below.

In certain embodiments, the change of the distance of the exit acoustic window can be accomplished by a sliding movement. However, in other embodiments of the present invention, in particular, if mechanical complex arrangements, the movement can be an exchange of mechanical elements.

In one embodiment, mechanical elements that are exchanged to achieve a change in wave front characteristics include the primary pressure pulse generating element, the focusing element, the reflecting element, the housing and the membrane. In another embodiment, the mechanical elements further include a closed fluid volume within the housing in which the pressure pulse is formed and transmitted through the exit window.

In one embodiment, the apparatus of the present invention is used in combination therapy. Here, the characteristics of waves emitted by the apparatus are switched from, for example, focused to divergent or from divergent with lower energy density to divergent with higher energy density. Thus, effects of a pressure pulse treatment can be optimized by using waves having different characteristics and/or energy densities, respectively.

While the above described universal toolbox of the present invention provides versatility, the person skilled in the art will appreciate that apparatuses that only produce waves having, for example, nearly plane characteristics, are less mechanically demanding and fulfill the requirements of many users.

As the person skilled in the art will also appreciate that embodiments shown in drawings 1a-1c and 2a-2c are independent of the generation principle and thus are valid for not only electro-hydraulic shock wave generation but also for, but not limited to, PP/SW generation based on electromagnetic, piezoceramic and ballistic principles. The pressure pulse generators may, in certain embodiments, be equipped with a water cushion that houses water which defines the path of pressure pulse waves that is, through which those waves are transmitted. In a preferred embodiment, a patient is coupled via ultrasound gel or oil to the acoustic exit window (17), which can, for example, be an acoustic transparent membrane, a water cushion, a plastic plate or a metal plate.

Figure 3:
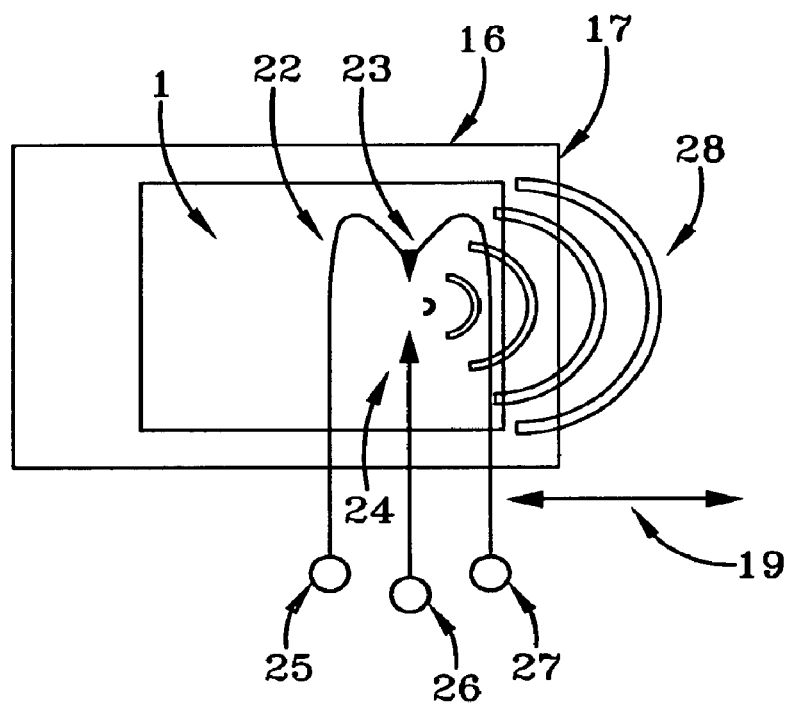
FIG. 3 is a simplified depiction of an electro-hydraulic pressure pulse/shock wave generator having no reflector or focusing element. Thus, the waves of the generator did not pass through a focusing element prior to exiting it.

FIG. 3 is a simplified depiction of the pressure pulse/shock wave apparatus having no focusing reflector or other focusing element. The generated waves emanate from the apparatus without coming into contact with any focusing elements. FIG. 3 shows, as an example, an electrode as a pressure pulse generating element producing divergent waves (28) behind the ignition point defined by a spark between the tips of the electrode (23, 24).

Figure 4A:
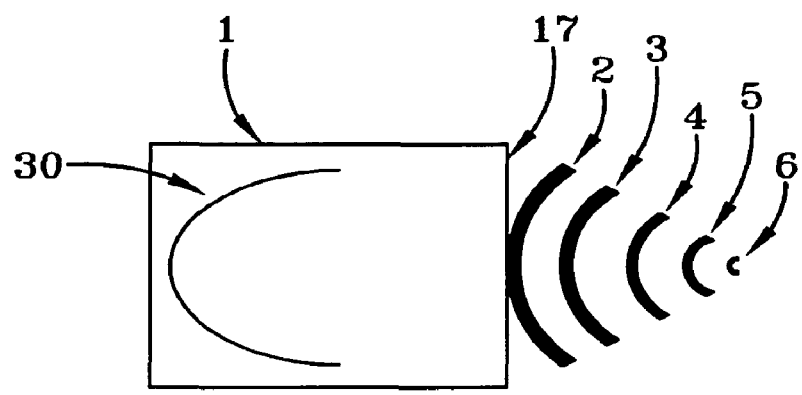
FIG. 4a is a simplified depiction of a pressure pulse/shock wave generator having a focusing element in the form of an ellipsoid. The waves generated are focused.

FIG. 4a is a simplified depiction of the pressure pulse/shock wave generator (shock wave head) having as focusing element an ellipsoid (30). Thus, the generated waves are focused at (6).

Figure 4B:
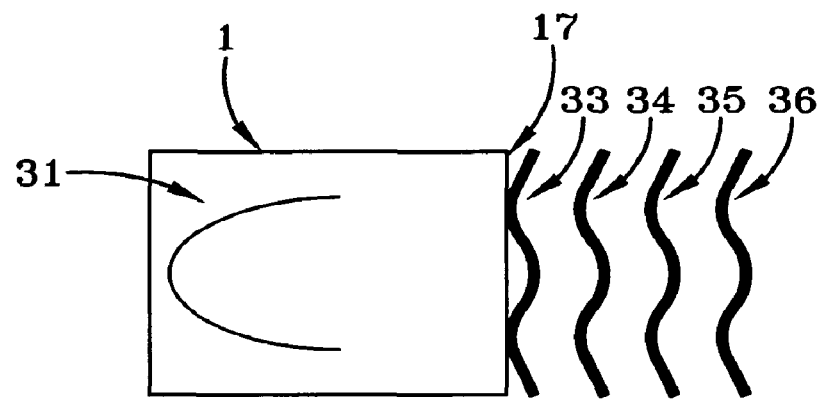
FIG. 4b is a simplified depiction of a pressure pulse/shock wave generator having a parabolic reflector element and generating waves that are disturbed plane.

FIG. 4b is a simplified depiction of the pressure pulse/shock wave generator (shock wave head) having as a focusing element an paraboloid ($y^2=2px$). Thus, the characteristics of the wave fronts generated behind the exit window (33, 34, 35, and 36) are disturbed plane ("parallel"), the disturbance resulting from phenomena ranging from electrode burn down, spark ignition spatial variation to diffraction effects. However, other phenomena might contribute to the disturbance.

Figure 4C:
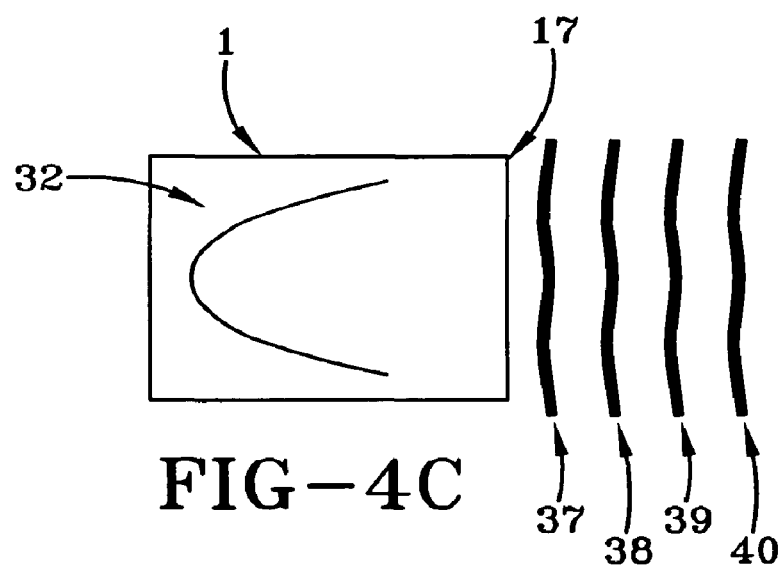
FIG. 4c is a simplified depiction of a pressure pulse/shock wave generator having a quasi parabolic reflector element (generalized paraboloid) and generating waves that are nearly plane/have nearly plane characteristics.

FIG. 4c is a simplified depiction of the pressure pulse/shock wave generator (shock wave head) having as a focusing element a generalized paraboloid ($y^n=2px$, with $1,2<n<2,8$ and $n\neq 2$). Thus, the characteristics of the wave fronts generated behind the exit window (37, 38, 39, and 40) are, compared to the wave fronts generated by a paraboloid ($y^2=2px$), less disturbed, that is, nearly plane (or nearly parallel or nearly even (37, 38, 39, 40)). Thus, conformational adjustments of a regular paraboloid ($y^2=2px$) to produce a generalized paraboloid can compensate for disturbances from, e.g., electrode burn down. Thus, in a generalized paraboloid, the characteristics of the wave front may be nearly plane due to its ability to compensate for phenomena including, but not limited to, burn down of the tips of the electrode and/or for disturbances caused by diffraction at the aperture of the paraboloid. For example, in a regular paraboloid ($y^2=2px$) with p=1.25, introduction of a new electrode may result in p being about 1.05. If an electrode is used that adjusts itself to maintain the distance between the electrode tips ("adjustable electrode") and assuming that the electrodes burn down is 4 mm (z=4 mm), p will increase to about 1.45. To compensate for this burn down, and here the change of p, and to generate nearly plane wave fronts over the life span of an electrode, a generalized paraboloid having, for example n=1.66 or n=2.5 may be used. An adjustable electrode is, for example, disclosed in U.S. Pat. No. 6,217,531.

Figure 4D:
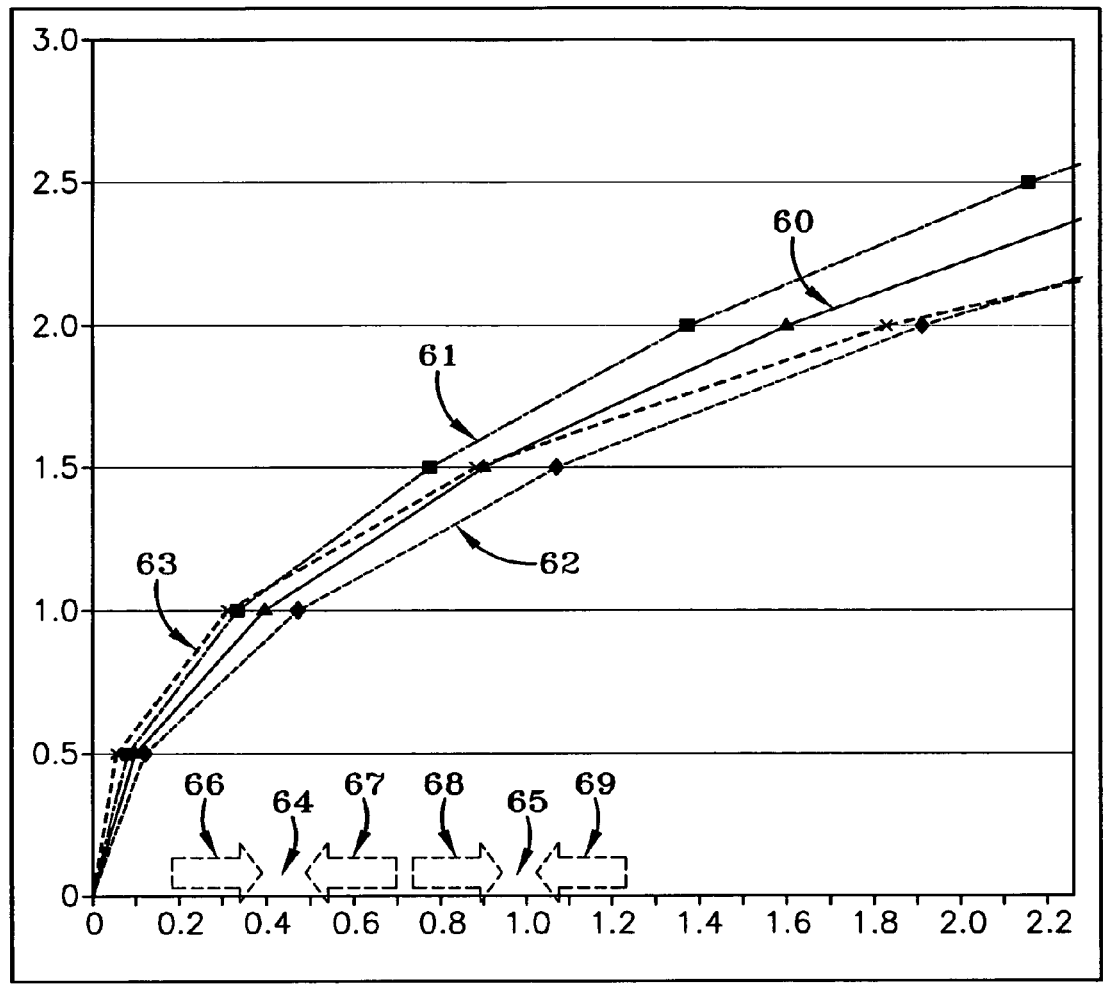
FIG. 4d is a simplified depiction of a generalized paraboloid with better focusing characteristic than a paraboloid in which n=2. The electrode usage is shown. The generalized paraboloid, which is an interpolation (optimization) between two optimized paraboloids for a new electrode and for a used (burned down) electrode is also shown.

FIG. 4d shows sectional views of a number of paraboloids. Numeral 62 indicates a paraboloid of the shape $y^2=2px$ with p=0.9 as indicated by numeral 64 at the x axis which specifies the p/2 value (focal point of the paraboloid). Two electrode tips of a new electrode 66 (inner tip) and 67 (outer tip) are also shown in the Figure. If the electrodes are fired and the tips are burning down the position of the tips change, for example, to position 68 and 69 when using an electrode which adjusts its position to compensate for the tip burn down. In order to generate pressure pulse/shock waves having nearly plane characteristics, the paraboloid has to be corrected in its p value. The p value for the burned down electrode is indicate by 65 as p/2=1. This value, which constitutes a slight exaggeration, was chosen to allow for an easier interpretation of the Figure. The corresponding paraboloid has the shape indicated by 61, which is wider than paraboloid 62 because the value of p is increased. An average paraboloid is indicated by numeral 60 in which p=1.25 cm. A generalized paraboloid is indicated by dashed line 63 and constitutes a paraboloid having a shape between paraboloids 61 and 62. This particular generalized paraboloid was generated by choosing a value of $n\neq 2$ and a p value of about 1.55 cm. The generalized paraboloid compensates for different p values that result from the electrode burn down and/or adjustment of the electrode tips.

Figure 5:
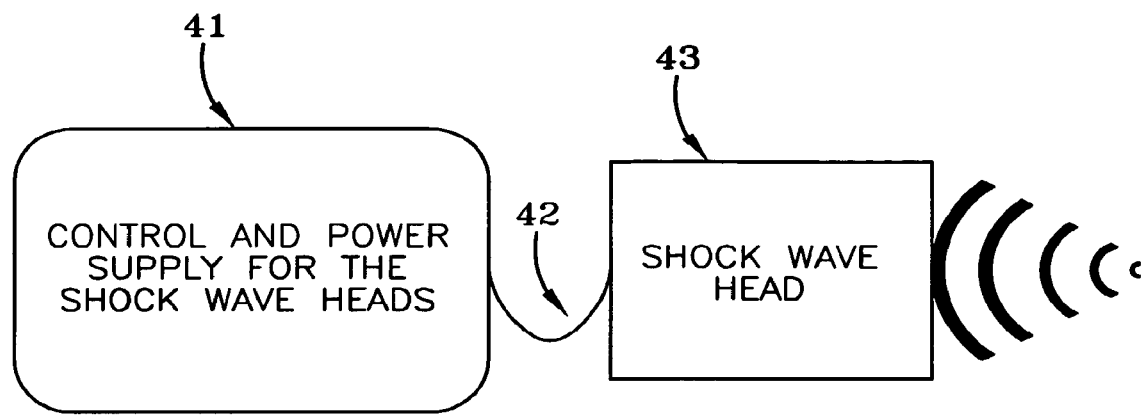
FIG. 5 is a simplified depiction of a pressure pulse/shock wave generator being connected to a control/power supply unit.

FIG. 5 is a simplified depiction of a set-up of the pressure pulse/shock wave generator (43) (shock wave head) and a control and power supply unit (41) for the shock wave head (43) connected via electrical cables (42) which may also include water hoses that can be used in the context of the present invention. However, as the person skilled in the art will appreciate, other set-ups are possible and within the scope of the present invention.

Figure 6:
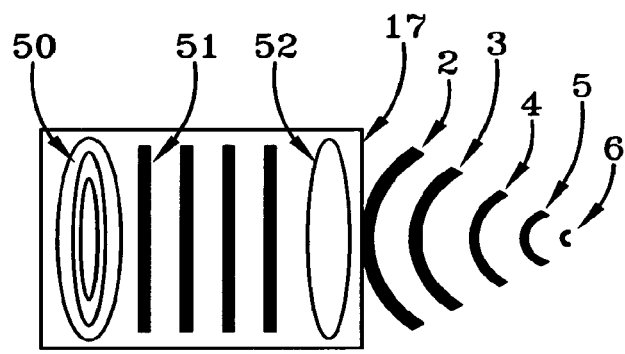
FIG. 6 is a simplified depiction of a pressure pulse/shock wave generator comprising a flat EMSE (electromagnetic shock wave emitter) coil system to generate nearly plane waves as well as an acoustic lens. Convergent wave fronts are leaving the housing via an exit window.

FIG. 6 is a simplified depiction of the pressure pulse/shock wave generator (shock wave head) having an electromagnetic flat coil 50 as the generating element. Because of the plane surface of the accelerated metal membrane of this pressure pulse/shock wave generating element, it emits nearly plane waves which are indicated by lines 51. In shock wave heads, an acoustic lens 52 is generally used to focus these waves. The shape of the lens might vary according to the sound velocity of the material it is made of. At the exit window 17 the focused waves emanate from the housing and converge towards focal point 6.

Figure 7:
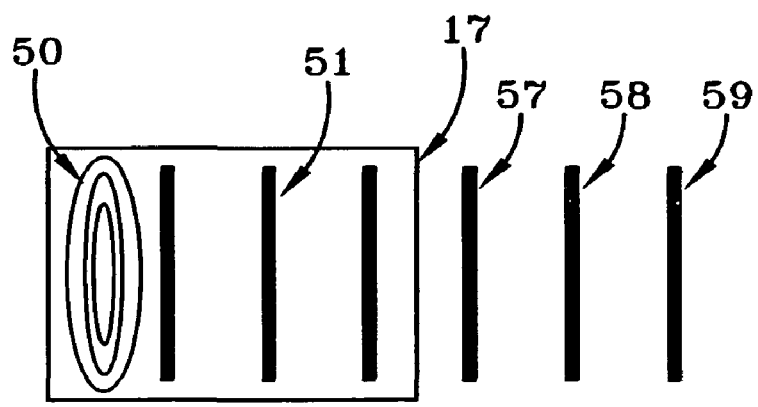
FIG. 7 is a simplified depiction of a pressure pulse/shock wave generator having a flat EMSE coil system to generate nearly plane waves. The generator has no reflecting or focusing element. As a result, the pressure pulse/shock waves are leaving the housing via the exit window unfocused having nearly plane wave characteristics.

FIG. 7 is a simplified depiction of the pressure pulse/shock wave generator (shock wave head) having an electromagnetic flat coil 50 as the generating element. Because of the plane surface of the accelerated metal membrane of this generating element, it emits nearly plane waves which are indicated by lines 51. No focusing lens or reflecting lens is used to modify the characteristics of the wave fronts of these waves, thus nearly plane waves having nearly plane characteristics are leaving the housing at exit window 17.

Figure 8:
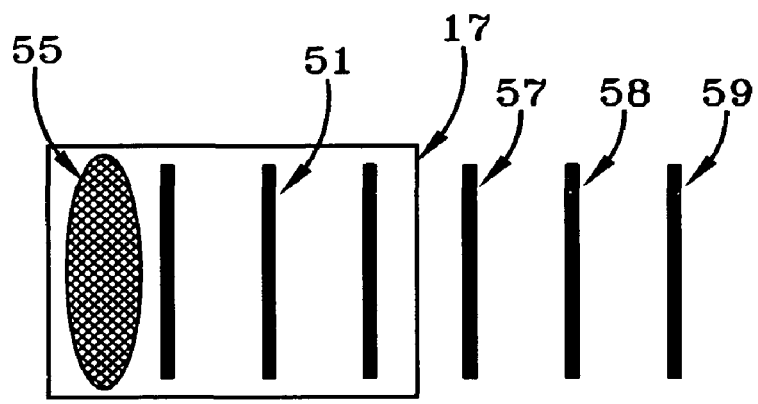
FIG. 8 is a simplified depiction of a pressure pulse/shock wave generator having a flat piezoceramic plate equipped with a single or numerous individual piezoceramic elements to generate plane waves without a reflecting or focusing element. As a result, the pressure pulse/shock waves are leaving the housing via the exit window unfocused having nearly plane wave characteristics.

FIG. 8 is a simplified depiction of the pressure pulse/shock wave generator (shock wave head) having an piezoceramic flat surface with piezo crystals 55 as the generating element. Because of the plane surface of this generating element, it emits nearly plane waves which are indicated by lines 51. No focusing lens or reflecting lens is used to modify the characteristics of the wave fronts of these waves, thus nearly plane waves are leaving the housing at exit window 17. Emitting surfaces having other shapes might be used, in particular curved emitting surfaces such as those shown in FIGS. 4a to 4c as well as spherical surfaces. To generate waves having nearly plane or divergent characteristics, additional reflecting elements or lenses might be used. The crystals might, alternatively, be stimulated via an electronic control circuit at different times, so that waves having plane or divergent wave characteristics can be formed even without additional reflecting elements or lenses.

Figure 9:
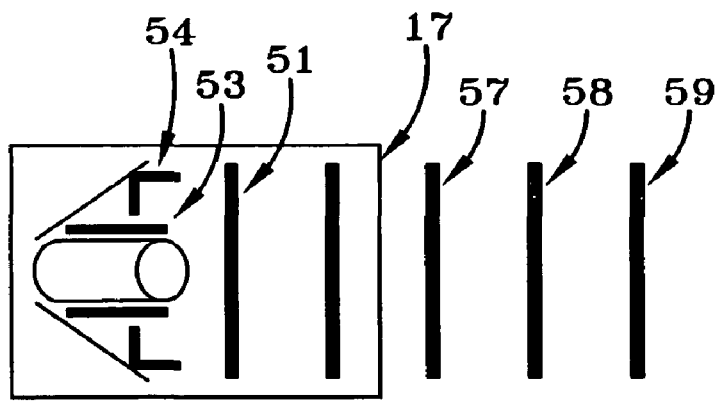
FIG. 9 is a simplified depiction of a pressure pulse/shock wave generator having a cylindrical EMSE system and a triangular shaped reflecting element to generate plane waves. As a result, the pressure pulse/shock waves are leaving the housing via the exit window unfocused having nearly plane wave characteristics.

FIG. 9 is a simplified depiction of the pressure pulse/shock wave generator (shock wave head) comprising a cylindrical electromagnet as a generating element 53 and a first reflector having a triangular shape to generate nearly plane waves 54 and 51. Other shapes of the reflector or additional lenses might be used to generate divergent waves as well.

Figure 10:
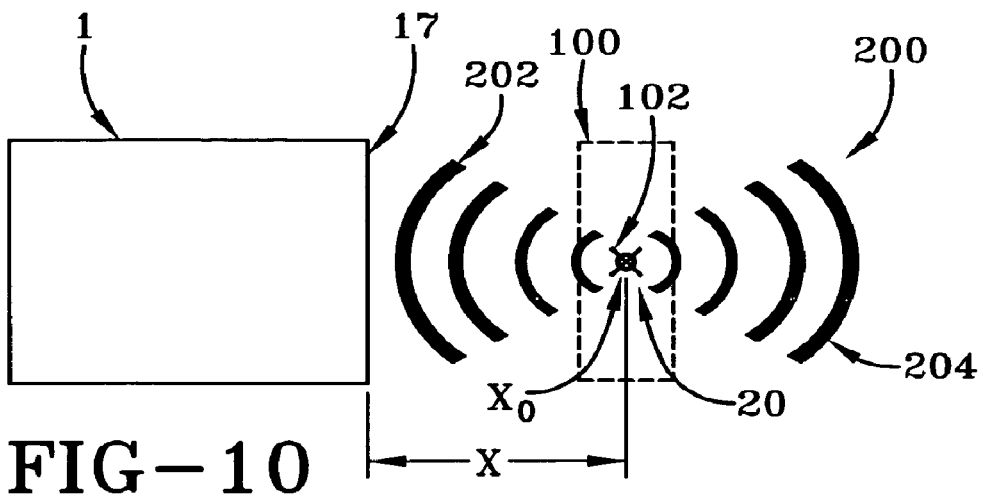
FIG. 10 is a simplified depiction of a pressure pulse/shock wave (PP/SW) generator with focusing wave characteristics shown focused with the focal point or geometrical focal volume being on a substance, the focus being targeted on the location $X_0$.
Figure 11:
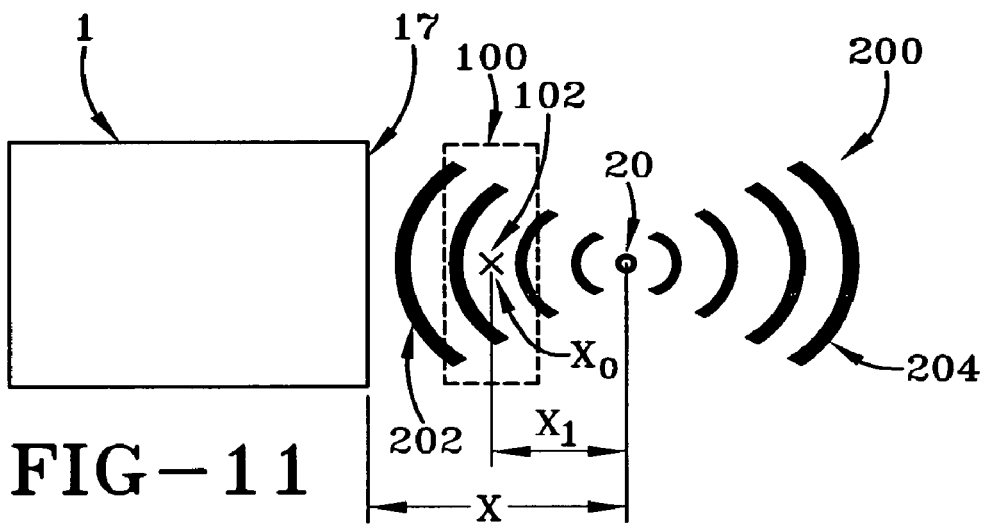
FIG. 11 is a simplified depiction of a pressure pulse/shock wave (PP/SW) generator with the focusing wave characteristics shown wherein the focus is located a distance $X_1$ from the location $X_0$ of a substance wherein the converging waves impinge the substance.
Figure 12:
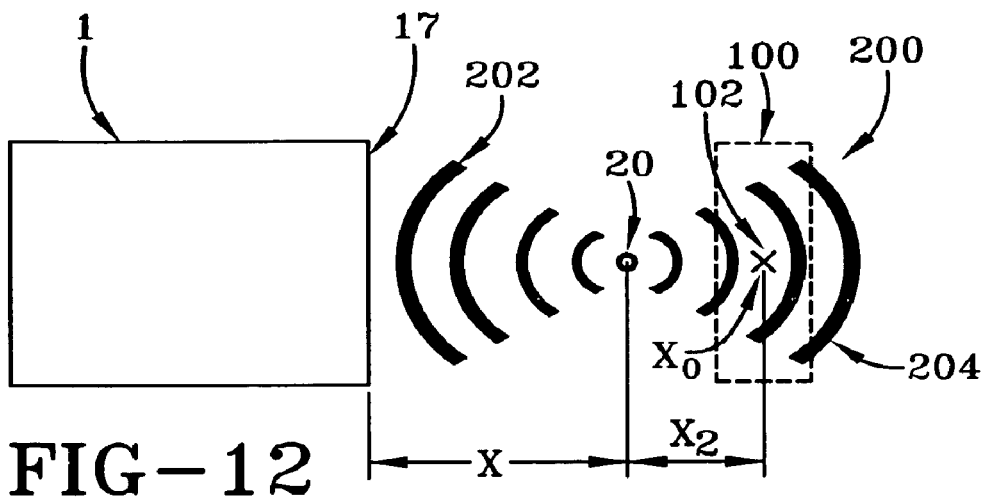
FIG. 12 is a simplified depiction of a pressure pulse/shock wave (PP/SW) generator with focusing wave characteristics shown wherein the focus is located a distance $X_2$ from the mass location $X_0$ wherein the emitted divergent waves impinge the substance.

With reference to FIGS. 10, 11 and 12 a schematic view of a shock wave generator or source 1 is shown emitting a shock wave front 200 from an exit window 17. The shock wave front 200 has converging waves 202 extending to a focal point or focal geometric volume 20 at a location spaced a distance X from the generator or source 1. Thereafter the wave front 200 passes from the focal point or geometric volume 20 in a diverging wave pattern as has been discussed in the various other FIGS. 1-9 generally.

With particular reference to FIG. 10 a substance 100 is shown generally centered on the focal point or volume 20 at a location $X_0$ within the substance 100. In this orientation the emitted waves are focused and thus are emitting a high intensity acoustic energy at the location $X_0$. This location $X_0$ can be anywhere within or on the substance. Assuming the substance 100 is a tissue having a mass 102 at location $X_0$ then the focus is located directly on the mass 102. In one method of treating a tumor or any other type mass 102 these focused waves can be directed to destroy or otherwise reduce the mass 102.

With reference to FIG. 11, the substance 100 is shifted a distance X toward the generator or source 1. The substance 100 at location $X_0$ being positioned a distance $X-X_1$ from the source 1. This insures the substance 100 is impinged by converging waves 202 but removed from the focal point 20. When the substance 100 is tissue this bombardment of converging waves 202 stimulates the cells activating the desired healing response as previously discussed.

With reference to FIG. 12, the substance 100 is shown shifted or located in the diverging wave portion 204 of the wave front 200. As shown $X_0$ is now at a distance $X_2$ from the focal point or geometric volume 20 located at a distance X from the source 1. Accordingly $X_0$ is located a distance $X+X_2$ from the source 1. As in FIG. 10 this region of diverging waves 204 can be used to stimulate the substance 100 which when the substance is a cellular tissue stimulates the cells to produce the desired healing effect or response.

As shown the use of these acoustic wave forms can be used separately or in combination to achieve the desired therapeutic effect.

Furthermore such acoustic wave forms can be used in combination with drugs, chemical treatments, irradiation therapy or even physical therapy and when so combined the stimulated cells will more rapidly assist the body's natural healing response.

The present invention provides an apparatus for an effective treatment of indications, which benefit from low energy pressure pulse/shock waves having nearly plane or even divergent characteristics. For the treatment of those indications, the procedure to locate the area to which the pressure pulses/shock waves are applied often needs to be less accurate than, e.g., when kidney stones are destroyed with focused waves. In fact, sometimes the knowledge of the physique of the subject to be treated is sufficient, so that imaging devices like ultrasound, x-ray or similar, as they are known from devices used in the destruction of kidney stones, are not required. For certain indication, it might be advantageous to a treat an entire area simultaneously, for example if the affected tissue is spread out and has a more area like character rather than a volume like character. One example of such an indication is spread out muscle pain. The small focal points/focus volumes (defined as −6 dB of the maximum pressure amplitude at a certain energy output setting) of a few mm (for example 2-25 mm) produced by focused waves might be too small to optimally treat the affected area. The area of the focal point/focus volume can be enlarged by reducing the focusing or even by eliminating it all together by using an apparatus according to the present invention which produces waves having wave fronts with nearly plane or divergent characteristics.

With an unfocused wave having nearly plane wave characteristic or even divergent wave characteristics, the energy density of the wave may be or may be adjusted to be so low that side effects including pain are very minor or even do not exist at all.

In certain embodiments, the apparatus of the present invention is able to produce waves having energy density values that are below 0.1 mJ/mm2 or even as low as 0.000 001 mJ/mm2. In a preferred embodiment, those low end values range between 0.1-0.001 mJ/mm2. With these low energy densities, side effects are reduced and the dose application is much more uniform. Additionally, the possibility of harming surface tissue is reduced when using an apparatus of the present invention that generates waves having nearly plane or divergent characteristics and larger transmission areas compared to apparatuses using a focused shock wave source that need to be moved around to cover the affected area. The apparatus of the present invention also may allow the user to make more precise energy density adjustments than an apparatus generating only focused shock waves, which is generally limited in terms of lowering the energy output.

The treatment of the above mentioned indications are believed to be a first time use of acoustic shock wave therapy generally with the exception of the heart and pancreas which have been subjected to tissue focal point targeted by focused shock waves. None of the work done to date has treated the above mentioned indications with convergent, divergent, planar or near-planar acoustic shock waves of low energy. Accordingly the use of acoustic shock waves for treating such indications as cirrhosis of the liver, cancer, myelodysplasia, stomach ulcers, AIDs, Alzheimer's disease, bone cancer, arthritis, emphysema, gout, rheumatic disease, HIV, leprosy, lupus, skin sarcomas, cellulitis, melanomas, osteoporosis, periodontal diseases, pseudoarthrosis, wounds, scars, acne, burns, diabetes, cystic fibrosis, nerve paraplegia or enhancing stem cell reactions are completely new and a breakthrough in medical treatments of such diseases. As is the use of acoustic shock waves for germicidal wound cleaning or preventive medical treatments.

It will be appreciated that the apparatuses and processes of the present invention can have a variety of embodiments, only a few of which are disclosed herein. It will be apparent to the artisan that other embodiments exist and do not depart from the spirit of the invention. Thus, the described embodiments are illustrative and should not be construed as restrictive.

What is claimed is:

1. The method of stimulating a cellular substance wherein the cellular substance is a tissue having cells and the tissue is either part of an organ or the entire organ of a human or animal comprises the steps of:

treating the cellular substance;

activating an acoustic shock wave generator or source to emit pressure pulses or acoustic shock waves directed toward the substance to impinge the substance with pressure pulses or shock waves having a low energy density in the range of 0.00001 mJ/mm$^2$ to 1.0 mJ/mm$^2$; the pressure pulse being an acoustic pulse which includes several cycles of positive and negative pressure, wherein the pressure pulse has an amplitude of the positive part of such a cycle should be above 0.1 MPa and the time duration of the pressure pulse is from below a microsecond to about a second, rise times of the positive part of the first pressure cycle in the range of nano-seconds (ns) up to some milli-seconds (ms), the acoustic shock waves being very fast pressure pulses having amplitudes above 0.1 MPa and rise times of the amplitude being below 100's of ns, the duration of the shock wave is typically below 1-3 micro-seconds (μs) for the positive part of a cycle and typically above some micro-seconds for the negative part of a cycle; and subjecting the cellular substance to convergent, divergent, planar or near planar acoustic shock waves or pressure pulses in the absence of a focal point impinging the substance stimulating a cellular response in the absence of creating cavitation bubbles evidenced by not experiencing the sensation of cellular hemorrhaging caused by the emitted waves or pulses in the substance wherein the cellular substance is positioned within a path of the emitted shock waves or pressure pulses and away from any localized geometric focal volume or point of the emitted shock waves wherein the emitted shock waves or pressure pulses either have no geometric focal volume or point or have a focal volume or point ahead of the cellular substance or beyond the cellular substance thereby passing the emitted waves through the cellular substance while avoiding having any localized focal point within the cellular substance wherein the emitted pressure pulses or shock waves are convergent, divergent, planar or near planar and the pressure pulse shock wave generator or source is based on electro-hydraulic, electromagnetic, piezoceramic or ballistic wave generation having an energy density value ranging as low as 0.00001 mJ/mm$^2$ to a high end of below 1.0 mJ/mm$^2$.

2. The method of stimulating a substance of claim 1 wherein the emitted shock waves are divergent or near planar, or wherein the emitted shock waves are convergent having a geometric focal volume or point at a distance of at least X from the generator or source, the method further comprising positioning the substance at a distance less than the distance X from the source.

3. The method of stimulating a substance of claim 1 wherein the organ is either a heart, a brain, skin, a live or a kidney.

4. The method of stimulating a substance of claim 3 wherein the step of subjecting the substance to acoustic shock waves includes the step of treating cirrhosis of the liver.

5. The method of stimulating a substance of claim 3 wherein the substance has an indication of myelodysplasia.

6. The method of stimulating a substance of claim 1 wherein the step of subjecting the substance to acoustic shock waves includes the step of correcting a pathological growth of the epiphysial plate.

7. The method of stimulating a substance of claim 1 wherein the step of subjecting the substance to acoustic shock waves includes killing bacteria by destroying bacterial cell membranes or stimulating a biological defense mechanism within said substance by exposure to the acoustic shock waves.

8. The method of stimulating a substance of claim 1 wherein the substance includes one or more vertebrae.

9. The method of stimulating a substance of claim 1 wherein the substance is the stomach and wherein the stomach has one or more stomach ulcers.

10. The method of stimulating a substance of claim 1 wherein the substance further includes a joint and surrounding tissue.

11. The method of stimulating a substance of claim 10 wherein the substance has an indication of arthritis.

12. The method of stimulating a substance of claim 10 wherein the substance has an indication of gout.

13. The method of stimulating a substance of claim 1 wherein the substance has an indication of rheumatic disease and wherein the rheumatic disease is Lupus.

14. The method of stimulating a substance of claim 1 wherein the step of subjecting the substance to acoustic shock waves includes the step of treating osteoporosis.

15. The method of stimulating a substance of claim 1 wherein the step of subjecting the substance to acoustic shock waves includes the step of treating pseudoarthrosis.

16. The method of stimulating a substance of claim 1 wherein the step of subjecting the substance to acoustic shock waves includes the step of treating HIV.

17. The method of stimulating a substance of claim 1 wherein the step of subjecting the substance to acoustic shock waves includes the step of treating periodontal diseases.

18. The method of stimulating a substance of claim 1 wherein the step of subjecting the substance to acoustic shock waves includes the step of treating emphysema.

19. The method of stimulating a cellular substance wherein the cellular substance is a placenta having stem cells, or a patient having stem cells or a culture of stem cells comprises the steps of:

treating the cellular substance;

activating an acoustic shock wave generator or source to emit pressure pulses or acoustic shock waves directed toward the substance to impinge the substance with pressure pulses or shock waves having a low energy density in the range of 0.00001 mJ/mm$^2$ to 1.0 mJ/mm$^2$; the pressure pulse being an acoustic pulse which includes several cycles of positive and negative pressure, wherein the pressure pulse has an amplitude of the positive part of such a cycle should be above 0.1 MPa and the time duration of the pressure pulse is from below a microsecond to about a second, rise times of the positive part of the first pressure cycle in the range of nano-seconds (ns) up to some milli-seconds (ms), the acoustic shock waves being very fast pressure pulses having amplitudes above 0.1 MPa and rise times of the amplitude being below 100's of ns, the duration of the shock wave is typically below 1-3 micro-seconds (μs) for the positive part of a cycle and typically above some micro-seconds for the negative part of a cycle; and subjecting the cellular substance to convergent, divergent, planar or near planar acoustic shock waves or pressure pulses in the absence of a focal point impinging the substance stimulating a cellular response in the absence of creating cavitation bubbles evidenced by not experiencing the sensation of cellular hemorrhaging caused by the emitted waves or pulses in the substance wherein the cellular substance is positioned within a path of the emitted shock waves or pressure pulses and away from any localized geometric focal volume or point of the emitted shock waves wherein the emitted shock waves or pressure pulses either have no geometric focal volume or point or have a focal volume or point ahead of the cellular substance or beyond the cellular substance thereby passing the emitted waves through the cellular substance while avoiding having any localized focal point within the cellular substance wherein the emitted pressure pulses or shock waves are convergent, divergent, planar or near planar and the pressure pulse shock wave generator or source is based on electro-hydraulic, electromagnetic, piezoceramic or ballistic wave generation having an energy density value ranging as low as 0.00001 mJ/mm$^2$ to a high end of below 1.0 mJ/mm$^2$.

20. The method of stimulating a substance of claim 19 wherein the shock waves stimulate the stem cells enhancing replication.

* * * * *